United States Patent
Weferling et al.

(10) Patent No.: US 6,770,779 B1
(45) Date of Patent: Aug. 3, 2004

(54) PROCESS FOR PREPARING ALKYLPHOSPHONITE ESTERS

(75) Inventors: Norbert Weferling, Hürth (DE); Martin Sicken, Köln (DE); Hans-Peter Schmitz, Brühl (DE); Günter Kolbe, Kerpen-Türnich (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/577,464

(22) Filed: May 24, 2000

(30) Foreign Application Priority Data

May 25, 1999 (DE) ......................................... 199 23 615

(51) Int. Cl.$^7$ .............................. C07F 9/28; C07F 9/32; C07F 9/22
(52) U.S. Cl. ........................... 562/8; 558/89; 558/104; 568/8; 524/133
(58) Field of Search ............................... 562/8; 558/89, 558/104; 568/8; 524/133

(56) References Cited

U.S. PATENT DOCUMENTS

| | | | |
|---|---|---|---|
| 2,724,718 A | * 11/1955 | Stiles et al. ................. | 558/137 |
| 2,957,931 A | 11/1960 | Hamilton et al. | |
| 3,316,293 A | 4/1967 | Carr et al. | |
| 3,579,576 A | 5/1971 | Angstadt | |
| 4,379,132 A | * 4/1983 | Annarelli et al. ........... | 423/305 |
| 4,521,348 A | 6/1985 | Finke et al. | |
| 5,973,194 A | * 10/1999 | Weferling et al. ............. | 562/8 |
| 6,011,172 A | * 1/2000 | Weferling et al. ............. | 562/8 |
| 6,090,967 A | * 7/2000 | Horold et al. ............... | 558/105 |
| 6,090,968 A | * 7/2000 | Horold et al. ............... | 558/137 |
| 6,232,493 B1 | * 5/2001 | Weferling et al. ............. | 562/8 |
| 6,242,642 B1 | * 6/2001 | Weferling et al. ............. | 562/8 |
| 6,278,012 B1 | * 8/2001 | Horold et al. ............... | 558/110 |
| 6,300,516 B1 | * 10/2001 | Weferling et al. ............. | 562/8 |
| 6,329,544 B1 | * 12/2001 | Weferling et al. ............. | 562/8 |
| 6,355,832 B1 | * 3/2002 | Weferling et al. ............. | 562/8 |
| 6,359,171 B1 | * 3/2002 | Weferling et al. ............. | 562/8 |
| 6,420,598 B1 | * 7/2002 | Weferling et al. ............. | 562/8 |
| 6,583,315 B2 | * 6/2003 | Sicken et al. ................ | 562/20 |

FOREIGN PATENT DOCUMENTS

| | | |
|---|---|---|
| EP | 0 011 245 | 5/1980 |
| EP | 0 969 008 | 1/2000 |
| EP | 0 969 009 | 1/2000 |
| WO | WO 99/28326 | 6/1999 |

OTHER PUBLICATIONS

EPO Search Report Sep. 14, 2000.
EPO Search Report Jan. 30, 2001.
Houben–Werl, vol. 12/1, p306.
"Superbase–Induced Generation of Phosphide and Phosphinire Ions as Applied in Organic Synthesis", B.A. Trofimov et al., *Phosphor, Sulfur, and Silicon*, vol. 55 pp. 271–274, 1991.
Albracht S, et al., "The reaction properties of the txtraphosphorus molecule, The direct synthesis of oxganophosphorus compounds." XP000861829, 1992 vol. 42, p12–16.
Trofimov, Borls, et al., Phosphorus, Sulfur and Solicob, 1996, vol. 109–110, pp601–604, Generation of Phosphide Anions from Phosphorus Red and Phorphine in Strongly Basic Systems to Form Oxganylphosines and –Oxides, Oversean Publishers Association.
Semenzin, Delphine, et al., Tetrahedron Letters, 1994, vol. 35, No. 20, pp3297–3300, Alkylation of Phosphine PH3 Generated from Red Phosphorus, Elsevier Science Ltd.

* cited by examiner

*Primary Examiner*—Joseph D. Anthony
(74) *Attorney, Agent, or Firm*—Anthony A. Bisulca

(57) ABSTRACT

The present invention relates to a process for the preparation of alkylphosphonous acid esters which comprises a) reacting elemental yellow phosphorus with alkylating agents in the presence of a base to give a mixture which comprises, as principal constituents, the (metal) salts of alkylphosphonous, phosphorous and hypophosphorous acids, b) esterifying the principal constituents of the mixture from a) to give an ester mixture, c) isolating the ester of the alkylphosphonous acid from the ester mixture.

The invention likewise relates to the use of the alkylphosphonous acid esters prepared by this process as precursors for further syntheses, inter alia for the preparation of crop protection agents.

22 Claims, No Drawings

PROCESS FOR PREPARING ALKYLPHOSPHONITE ESTERS

BACKGROUND OF THE INVENTION

The present invention relates to a process for the preparation of alkylphosphonous acid esters and to the use of the products prepared by this process.

Alkylphosphonous acid esters are valuable synthetic building blocks which can be employed, for example, for the preparation of crop protection agents and flame retardants.

The preparation of these compounds is technically complex and has hitherto been carried out, in the case of the particularly interesting esters of methylphosphonous acid, from the corresponding phosphonous acid dihalides by reaction with alcohols or by hydrolysis of the phosphonous acid dihalides to the phosphonous acids followed by esterification.

The phosphonous acid dihalides on which both processes are based, such as, for example, methyldichlorophosphine, which is extremely difficult to handle, have hitherto been prepared in a complex synthesis from phosphorus trihalides and alkyl halides in the presence of aluminum chloride (Houben-Weyl, Volume 12/1, p. 306). The reaction is highly exothermic and can only be controlled with difficulty in industry. In addition, various by-products are formed which, like some of the above-mentioned starting materials, are toxic, self-igniting and/or corrosive, i.e. are highly undesirable.

SUMMARY OF THE INVENTION

There is therefore a need for a process for the preparation of alkylphosphonous acid esters which can be carried out in a simple manner and in which uniform products are obtained in high yield. A process of this type should also be significantly superior to the processes known hitherto in economic and environmental terms.

The invention thus has the object of providing a process for the preparation of alkylphosphonous acid esters which avoids the above-mentioned disadvantages and, in particular, starts from easily handled, industrially available and readily controllable starting materials.

DESCRIPTION OF THE PREFERRED EMBODIMENTS

This object is achieved by a process of the type mentioned at the outset which comprises
a) reacting elemental yellow phosphorus with alkylating agents in the presence of a base to give a mixture which comprises, as principal constituents, the (metal) salts of alkylphosphonous, phosphorous and hypophosphorous acids,
b) esterifying the principal constituents of the mixture from a) to give an ester mixture,
c) isolating the ester of the alkylphosphonous acid from the ester mixture.

The process according to the invention has the considerable advantages over the processes known hitherto that it has a positive balance in the product distribution and at the same time avoids the phosphonous acid dihalide starting materials, which are regarded as undesired from various points of view.

The alkylating agents are preferably alkyl halides, dialkyl sulfates, trialkyl phosphates, dialkyl carbonates and/or formic acid ortho-esters.

The alkylating agents are particularly preferably methyl chloride, methyl bromide and/or dimethyl sulfate.

The bases are preferably hydroxides, carbonates, bicarbonates, amides, alkoxides and/or amine bases.

The reaction in step a) is preferably carried out in a two-phase system comprising aqueous alkali or alkaline-earth metal hydroxide or mixtures thereof and an organic solvent.

The organic solvents employed are preferably straight-chain or branched alkanes, alkyl-substituted aromatic solvents, water-immiscible or only partially water-miscible alcohols or ethers, alone or in combination with one another.

The organic solvent employed is particularly preferably toluene, alone or in combination with alcohols.

The reaction can, if desired, also be carried out in a non-aqueous system, for example by using solid sodium hydroxide or amines.

The reaction is preferably carried out in the presence of a phase-transfer catalyst.

The phase-transfer catalyst is preferably a tetraalkylphosphonium halide, triphenylalkylphosphonium halide or tetraorganylammonium halide.

The temperature during the reaction is preferably from −20 to +80° C.

The temperature is particularly preferably from 0 to 30° C.

The reaction is preferably carried out under a pressure of from 0 to 10 bar.

The process according to the invention is preferably carried out by suspending or dissolving the yellow phosphorus in a solvent or solvent mixture and then reacting it with an alkyl halide and a compound of the formula MOH or M'$(OH)_2$ or mixtures thereof, where M is an alkali metal and M' is an alkaline-earth metal.

The yellow phosphorus and the alkyl halide are preferably reacted with one another in a molar ratio of from 1:1 to 1:3, where the molar ratio of yellow phosphorus to the compound of the formula MOH or M'$(OH)_2$ is from 1:1 to 1:5.

The principal constituents of the mixture from a) are preferably esterified in step b) using a linear or branched alcohol of the general formula R-OH, where R is a linear or branched alkyl radical having 1 to 10 carbon atoms.

In another preferred embodiment of the process according to the invention, the principal constituents of the mixture from a) are converted into a mixture of alkylphosphonous, phosphorous and hypophosphorous acids using mineral acids, with the (metal) salts of the mineral acids simultaneously being precipitated, and the mixture of these acids subsequently being esterified.

The water formed during the esterification is preferably removed by azeotropic distillation.

In other words, the esterification of the phosphonous acid to the corresponding monoester can be achieved by reaction with relatively high-boiling alcohols with removal of the resultant water by azeotropic distillation.

The precipitation of the metal salts, usually the alkali or alkaline-earth metal mineral salts, is preferably carried out here by replacement of the solvent water by the alcohol to be used in reaction step b).

The alkali or alkaline-earth metal mineral salt which has already precipitated is preferably filtered off before the esterification.

The alcohol is preferably n- or i-butanol, n-hexanol, ethylhexanol and/or amyl alcohol.

The mineral acid is preferably hydrochloric acid, sulfuric acid and/or phosphoric acid.

The mineral acid is particularly preferably hydrochloric acid.

The phosphines formed in small amounts during step a) are preferably removed by oxidation.

Hydrogen peroxide is preferably used as oxidant.

The ester of the alkylphosphonous acid is preferably removed by distillation in step c). The ester of the alkylphosphonous acid is preferably n-butyl methyl phosphonite, isobutyl methylphosphonite, n-hexyl methylphosphonite, 2-ethylhexyl methylphosphonite and/or amyl methylphosphonite.

The invention also relates to the use of the phosphonous acid esters prepared by the process according to the invention for the preparation of organophosphorus compounds.

The invention likewise relates to the use of the phosphonous acid esters prepared by the process according to the invention as precursors for chemical synthesis.

The invention also relates to the use of the phosphonous acid esters prepared by the process according to the invention for the preparation of phosphinic acids as starting materials for crop protection agents.

The invention also relates to the use of the phosphonous acid esters prepared by the process according to the invention as starting materials for the preparation of flame retardants.

The invention relates to the use of the phosphonous acid esters prepared by the process according to the invention as starting materials for the preparation of flame retardants for thermoplastic polymers, such as polyethylene terephthalate, polybutylene terephthalate or polyamide.

The invention also relates to the use of the phosphonous acid esters prepared by the process according to the invention as starting materials for the preparation of flame retardants for thermosetting resins, such as unsaturated polyester resins, epoxy resins, polyurethanes or acrylates.

Surprisingly, it has been found that elemental yellow phosphorus can, after step a) of the process according to the invention, be reacted with alkylating agents in a two-phase system (organic solvent/base) and, if desired, in the presence of a (phase-transfer) catalyst under extremely mild conditions to give the (metal) salt of the corresponding alkylphosphonous acid RP(:O)HOH.

In addition, small amounts of dialkylphosphinic acids, trialkylphosphine oxide $R_3P(:O)$, dialkylphosphine oxide and unidentified phosphorus compounds may be formed; these can be removed from the product mixture in the usual manner. A further by-product formed is hydrogen, which can easily be separated off from the reaction mixture. The above-mentioned dialkylphosphinic acids can be separated off from the reaction mixture and employed or further processed elsewhere.

Surprisingly, neither phosphine ($PH_3$) nor alkylphosphines ($RPH_2$, $R_2PH$) are formed in significant amounts in the process according to the invention. Through the choice of suitable reaction conditions—such as the addition of small amounts of alcohols to the organic phase—the formation of all unidentified phosphorus-containing by-products is minimized to a surprisingly low content of a few mol% of the yellow phosphorus employed, in favor of the main product, the (metal) salts of alkylphosphonous acid.

The process according to the invention can be carried out, for example, by initially introducing the solvent together with the phase-transfer catalyst and, if necessary, warming the mixture to above the melting point of the yellow phosphorus, then adding the elemental (yellow) phosphorus, cooling the mixture to temperatures of, for example, from −10 to +30° C. with vigorous stirring, and subsequently adding the alkylating agent. The reaction is initiated by addition of the base. When the reaction is complete, the reaction system can be diluted, for example with water, and the readily volatile components ($H_2$, $PH_3$, $RPH_2$, $R_2PH$ and excess alkylating agent, etc.) are subsequently removed.

This gives a base-containing/organic two phase system, whose phases are separated. The contents from the phases are determined analytically.

The reactants can also be combined in a different sequence, for example by introducing them continuously into a reactor (pressure tube, pressure reactor or cascade) in the above-defined molar ratio and removing them from the reactor again after a residence time of from 0.5 to 2 hours. The organic phase obtained after phase separation, which still contains the majority of any phase-transfer catalyst employed, is advantageously recycled.

The isolation of the pure alkylphosphonous acids from the mixture is carried out in a particularly simple manner via the corresponding esters, which, in contrast to the salts and acids of the alkylphosphonous acids, can be isolated from the mixture in a gentle manner by distillation. Although all other compounds present in the mixture are also partially esterified in steps b) and c) of the process according to the invention, they do not, however, form readily distillable products, and consequently the removal of the alkylphosphonous acid esters is achieved in surprisingly complete and pure form.

EXAMPLES

The invention is explained by the examples below:

Example 1

Ethylhexyl methylphosphonite a1) Reaction of yellow phosphorus with alkyl chloride

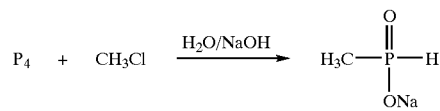

A solution of 26.1 g (0.05 mol) of tributylhexadecylphosphonium bromide in 1000 ml of toluene was introduced into a 5 l stainless-steel pressure reactor and pre-heated to 60° C. After 62 g (2 mol) of yellow phosphorus had been added, the mixture was cooled to −10° C. with vigorous stirring, and 202 g (4 mol) of methyl chloride were then condensed in. 400 g of 50% aqueous sodium hydroxide solution were then metered in over the course of 2 hours, during which the temperature was held at −10° C. 400 g of water were added over the course of a further hour, the mixture was then stirred for a further hour and warmed to room temperature, and the reactor was subsequently decompressed via combustion. Two homogeneous liquid phases were obtained, which were separated and analyzed.

The aqueous phase (weight: 920 g) contained 65.6 mol % of methylphosphonous acid, 14.9 mol % of phosphorous acid, 13.7 mol % of hypophosphorous acid and 2.8 mol % of dimethyphosphinic acid in the form of their sodium salts and 3 mol % of dimethylphosphine.

a2) Conversion of the sodium salts into the acids/NaCl removal

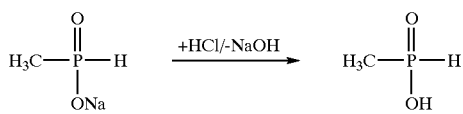

In succession, 60 g of 5% aqueous hydrogen peroxide solution (in order to remove the dimethylphosphine), 240 g of 36% hydrochloric acid and 400 g of 2-ethylhexanol were added to the solution. After the water formed had been removed by distillation on a water separator, the precipitated sodium chloride was filtered off and washed with 100 g of 2-ethylhexanol. The ethylhexanol solutions now contained the compounds mentioned under a) as the free acids.

b) Esterification of methanephosphonous acid in the reaction mixture:

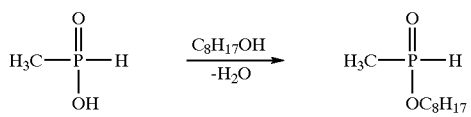

The ethylhexanol solutions from step a2) were combined and heated at about 120° C. for 6 hours on a water separator under slightly reduced pressure.

c). Isolation of the ester:

The esterified reaction mixture was subsequently freed from excess ethylhexanol by distillation and subjected to a vacuum distillation. At a pressure of 0.3 mm and a head temperature of 75° C., 220 g of 2-ethylhexyl methanephosphonite passed over. The product was obtained in the form of a clear, colorless liquid in a purity of greater than 99%, corresponding to a yield of 58%, based on the yellow phosphorus employed. Analyses: 16.0% of phosphorus (theory: 16.2%); $^{31}$P-NMR doublet at 34 ppm (diastereomer pair)

Example 2 n-Hexyl methylphosphonite 910 g of an aqueous phase comprising 67.4 mol % of methylphosphonous acid, 14.6 mol % of phosphorous acid, 8.7 mol % of hypophosphorous acid and 3.8 mol % of dimethylphosphinic acid in the form of their sodium salts and 4 mol % of dimethyldiphosphine were obtained analogously to the process in step a1) of Example 1. In succesion, 60 g of 5% aqueous hydrogen peroxide solution, 240 g of 36% hydrochloric acid and 300 g of n-hexanol were added to the solution. After the water present had been removed by distillation on a water separator, the precipitated sodium chloride was filtered off and washed with 100 g of n-hexanol. The hexanol solutions were combined and heated at about 140° C. for about 8 hours on a water separator. The esterified reaction mixture was subsequently freed from excess hexanol by distillation and subjected to a vacuum distillation. At a pressure of 0.3 mm and a head temperature of 62° C., 199 g of n-hexyl methanephosphonite passed over.

The product was obtained in the form of a clear, colorless liquid in a purity of greater than 99%, corresponding to a yield of 61%, based on the yellow phosphorus employed. Analyses: 18.5% of phosphorus (theory: 18.9%); $^{31}$P-NMR: singlet at 34 ppm.

Example 3 i-Butyl methylphosphonite 26.1 g (0.05 mol) of tributylhexadecylphosphonium bromide in 1000 ml of toluene were introduced into a 5 l stainless-steel pressure reactor and pre-heated to 60° C. After 62 g (2 mol) of yellow phosphorus had been added, the mixture was cooled to 50° C. with vigorous stirring, and 202 g (4 mol) of methyl chloride were then condensed in. The mixture was then warmed to about 20° C., and 500 g of 40% aqueous sodium hydroxide solution were metered in at this temperature over the course of 2 hours. 300 g of water were added over the course of one hour, the mixture was then stirred for a further two hours, and the reactor was subsequently decompressed via combustion. Two homogeneous liquid phases were obtained which were separated and analyzed.

The aqueous phase (weight: 920 g) comprised 64.6 mol % of methylphosphonous acid, 14.4 mol % of phosphorous acid, 12.7 mol % of hypophosphorous acid and 3.3 mol % of dimethylphosphinic acid in the form of their sodium salts and 5 mol % of dimethyldiphosphine. In succesion, 60 g of 5% aqueous hydrogen peroxide solution, 240 g of 36% hydrochloric acid and 300 g of isobutanol were added to the solution. After the water present had been removed by distillation on a water separator, the precipitated sodium chloride was filtered off and washed with 100 g of i-butanol. The butanol solutions were combined and heated at from 115 to 125° C. for about 12 hours on a water separator. The esterified reaction mixture was subsequently freed from excess butanol by distillation and subjected to a vacuum distillation. At a pressure of 0.5 mm and a head temperature of 42° C., 158 g of i-butyl methanephosphonite passed over.

The product was obtained in the form of a clear, colorless liquid in a purity of greater than 99%, corresponding to a yield of 58%, based on the yellow phosphorus employed. Analyses: 22.6% of phosphorus (theory: 22.8%); $^{31}$P-NMR: singlet at 34 ppm.

Example 4 n-Butyl methylphosphonite

The reaction of yellow phosphorus with methyl chloride/ 40% NaOH was carried out analogously to Example 3. The work-up was carried out using n-butanol.

The combined butanol solutions were heated at from 115 to 125° C. for about 14 hours on a water separator. The esterified reaction mixture was subsequently freed from excess butanol by distillation and subjected to a vacuum distillation. At a pressure of 0.5 mm and a head temperature of 42° C., 153 g of n-butyl methanephosphonite passed over.

The product was obtained in the form of a clear, colorless liquid in a purity of greater than 99%, corresponding to a yield of 56%, based on the yellow phosphorus employed. Analyses: 22.4% of phosphorus (theory: 22.8%); $^{31}$P-NMR: singlet at 34 ppm.

What is claimed is:

1. A process for the preparation of alkylphosphonous acid esters comprising the steps of:
   a) reacting elemental yellow phosphorus with alkylating agents in the presence of a base to give a mixture which comprises, as principal constituents, the (metal) salts of alkylphosphonous, phosphorous and hypophosphorous acids,
   b) esterifying the principal constituents of the mixture from a) to give an ester mixture, and
   c) isolating the ester of the alkylphosphonous acid from the ester mixture.

2. A process as claimed in claim 1, wherein the alkylating agents are alkyl halides, dialkyl sulfates, trialkyl phosphates, dialkyl carbonates or formic acid ortho-esters.

3. A process as claimed in claim 1, wherein the alkylating agent employed is methyl chloride, methyl bromide or dimethyl sulfate.

4. A process as claimed in claim 1, wherein the base is selected from the group consisting of hydroxides, carbonates, bicarbonates, amides, alkoxides and amine bases.

5. A process as claimed in claim 1, wherein the temperature during the reaction with the yellow phosphorus is from −20 to +80° C.

6. A process as claimed in claim 1, wherein the temperature during the reaction with the yellow phosphorus is from 0 to 30° C.

7. A process as claimed in claim 1, wherein the reaction is carried out under a pressure of from 0 to 10 bar.

8. A process as claimed in claim 1, wherein the principal constituents of the mixture from a) are esterified in step b) using a linear or branched alcohol of the general formula R—OH, where R is a linear or branched alkyl radical having 1 to 10 carbon atoms.

9. A process as claimed in claim 1, wherein the principal constituents of the mixture from a) are reacted with at least one mineral acid to give a mixture of alkylphosphonous, phosphorous and hypophosphorous acids and at the same time the (metal) salts of the mineral acids are precipitated, and the mixture of these acids is subsequently esterified.

10. A process as claimed in claim 1, wherein the water formed during the esterification is removed by azeotropic distillation.

11. A process as claimed in claim 1, wherein the at least one mineral acid is hydrochloric acid, sulfuric acid or phosphoric acid.

12. A process as claimed in claim 1, wherein the at least one mineral acid is hydrochloric acid.

13. A process as claimed in claim 1, wherein the ester of the alkylphosphonous acid is removed by distillation in step c).

14. A process as claimed in claim 1, wherein the ester of the alkylphosphonous acid is n-butyl methylphosphonite, isobutyl methylphosphonite, n-hexyl methylphosphonite, 2-ethylhexyl methylphosphonite or amyl methylphosphonite.

15. A process as claimed in claim 1, wherein the reaction in step a) is carried out in a two-phase system comprising aqueous alkali or alkaline-earth metal hydroxide or mixtures thereof and an organic solvent.

16. A process as claimed in claim 1, wherein the organic solvent employed is selected from the group consisting of straight-chain or branched alkanes, alkyl-substituted aromatic solvents water-immiscible or partially water-miscible alcohols or ethers, and combinations thereof.

17. A process as claimed in claim 15, wherein the organic solvent employed is toluene, alone or in combination with alcohols.

18. A process as claimed in claim 16, wherein the alcohol is n- or i-butanol, n-hexanol, ethylhexanol or amyl alcohol.

19. A process as claimed in claim 1, wherein the reaction is carried out in the presence of a phase-transfer catalyst.

20. A process as claimed in claim 19, wherein the phase-transfer catalyst is a tetraalkylphosphonium halide, triphenylalkylphosphonium halide or tetraorganylammonium halide.

21. A process as claimed in claim 1, wherein the phosphines formed in small amounts in step a) are removed by oxidation.

22. A process as claimed in claim 21, wherein hydrogen peroxide is employed for the oxidation.

* * * * *